United States Patent [19]

Yoshida et al.

[11] Patent Number: 4,500,536

[45] Date of Patent: Feb. 19, 1985

[54] DERIVATIVES OF N,N'-SUBSTITUTED AZOLECARBOXAMIDE AND AGRICULTURAL AND HORTICULTURAL FUNGICIDAL OR NEMATICIDAL COMPOSITION CONTAINING SAME AS ACTIVE INGREDIENTS

[75] Inventors: Hiroshi Yoshida, Urawa; Kengo Koike, Ageo; Shizuo Shimano, Ageo; Taizo Nakagawa, Ageo; Kaoru Ohmori, Okegawa, all of Japan

[73] Assignee: Nippon Kayaku Kabushiki Kaisha, Tokyo, Japan

[21] Appl. No.: 471,963

[22] Filed: Mar. 3, 1983

[30] Foreign Application Priority Data

Mar. 4, 1982 [JP] Japan .................................. 57-33040
Jul. 30, 1982 [JP] Japan ................................ 57-132023
Jan. 20, 1983 [JP] Japan .................................... 58-6691

[51] Int. Cl.$^3$ .................... A01N 43/50; A01N 43/56; A01N 43/64; C07D 231/10; C07D 233/54; C07D 249/08

[52] U.S. Cl. .................................. 514/397; 548/262; 548/336; 548/374; 514/383; 514/406

[58] Field of Search ...................... 548/262, 336, 374; 424/273 R, 273 P, 269

[56] References Cited

U.S. PATENT DOCUMENTS 3,308,131  3/1967  McKusick .......................... 548/262

Primary Examiner—Henry R. Jiles
Assistant Examiner—Kurt G. Briscoe
Attorney, Agent, or Firm—Henry C. Nields

[57] ABSTRACT

Disclosed herein are novel derivatives of N,N-substituted azolecarboxamide represented by the formula (I):

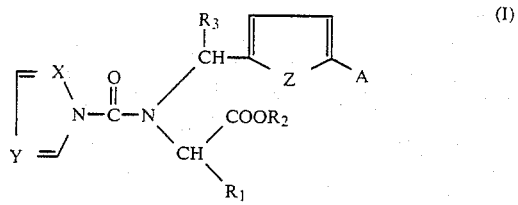

wherein $R_1$ represents a hydrogen atom, methyl group, ethyl group or propyl group; $R_2$ represents an alkyl group of 1 to 6 carbon atoms; $R_3$ represents a hydrogen atom or methyl group; A represents a hydrogen atom or methyl group; X and Y represent respectively a carbon atom or a nitrogen atom, provided that when X represents a nitrogen atom, Y represents a nitrogen atom or carbon atom and when X represents a carbon atom, Y represents a nitrogen atom; and Z represents an oxygen atom or sulfur atom, provided that when Z represents a sulfur atom, A represents only a hydrogen atom; and an agricultural or horticultural fungicidal or nematicidal composition containing the novel derivative of the formula (I) as an active ingredient.

12 Claims, No Drawings

DERIVATIVES OF N,N'-SUBSTITUTED AZOLECARBOXAMIDE AND AGRICULTURAL AND HORTICULTURAL FUNGICIDAL OR NEMATICIDAL COMPOSITION CONTAINING SAME AS ACTIVE INGREDIENTS

DETAILED DESCRIPTION

The present invention relates to novel derivatives of N,N-substituted azolecarboxamide (hereinafter referred to as the present compound) represented by the formula:

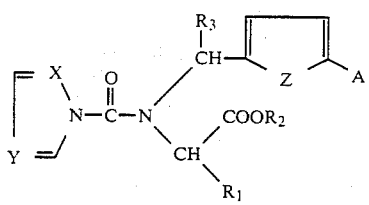

wherein $R_1$ represents a hydrogen atom, methyl group, ethyl group or propyl group; $R_2$ represents an alkyl group of 1 to 6 carbon atoms; $R_3$ represents hydrogen atom or methyl group; A represents a hydrogen atom or methyl group; X and Y represent respectively a carbon atom or nitrogen atom, provided that when X represents a nitrogen atom, Y represents a nitrogen atom or a carbon atom and when X represents a carbon atom, Y represents a nitrogen atom; and Z represents an oxygen atom or sulfur atom, provided that when Z represents sulfur atom, A represents only a hydrogen atom; and an agricultural or horicultural fungicidal composition or nematicidal composition containing one of the novel derivatives of N,N-azolecarboxamide as an active ingredient.

Hitherto, as fungicides used for protecting agricultural and horticultural plant from disease, organochlorine compounds, organosulfur compounds and gaseous compounds have been known and utilized. However, the organochlorine compounds have demerits of frequently giving phytotoxicity to crop plants and of frequently remaining in plant bodies and in soils due to the use thereof in higher concentrations because of the low effectiveness thereof. The organosulfur compounds have demerits of frequently giving phytotoxicity to crop plants and of causing contact dermatitis to the person handling thereof. In addition, the gaseous compounds have demerits of having an irritating odor and an unpleasant odor. As the nematicide, there have been so-called fumigants. However, the fumigants have demerits of frequently giving phytotoxicity to crop plants, of having an irritating or unpleasant odor and of not being applicable directly on plants.

The present inventors have found that the novel compound represented by the general formula (I) shows an extraordinary controlling effect on the crop diseases and the nematodes, for instance, Fusarium wilt, powdery mildew, scab, grey mold, rice blast, sheath blight of rice, brown spot of rice, Verticillium wilt, yellows, damping off, storage diseases of citrus, seed diseases, rice white-tip nematode, chrysanthemum foliar nematode, root-knot nematodes, lesion nematodes, cyst nematodes, pine wood nematode, etc. without showing the demerits of the fungicides, bactericides and nematocides hitherto known and used, and moreover, quite unexpectedly shows an extraordinary controlling effect on the diseases of the crop plants, for instance, powdery mildew, scab, grey mold, etc. by applying thereof into the soil where the crop plant has been grown, without giving and bad effects such as phytotoxicity to the crop plants, and the present inventors have completed the present invention.

The present compound is synthesized by either the process (A) or the process (B) as follows:

In the process (A), a carbamoyl halide represented by the formula (II) is brought into reaction with an azole represented by the formula (III), preferably in an inert solvent at a temperature of 50° to 150° C. for about 10 min to several hours to obtain the present compound:

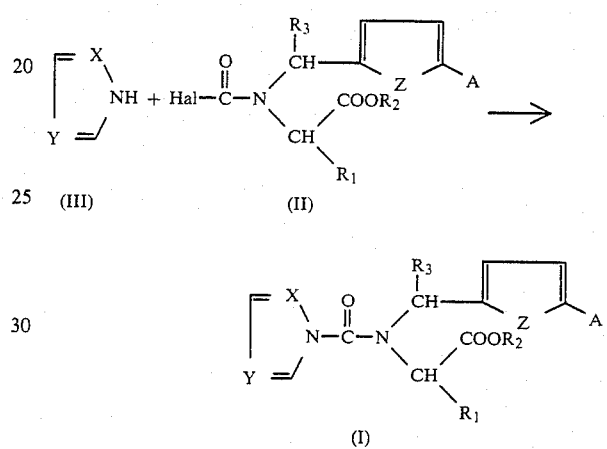

wherein $R_1$, $R_2$, $R_3$, A, X and Y are defined above and Hal represents a halogen atom.

A hydrogen halide generated during the reaction is preferably caught by a tertiary amine such as triethylamine, pyridine and the like or an excess of the azole represented by the formula (III).

In the process (B), a carbonylbisazole represented by the formula (IV) reacts with a secondary amine represented by the formula (V), preferably in an inert solvent at a temperature of 50° to 150° C. for about 10 min to several hours to obtain the present compound as follows:

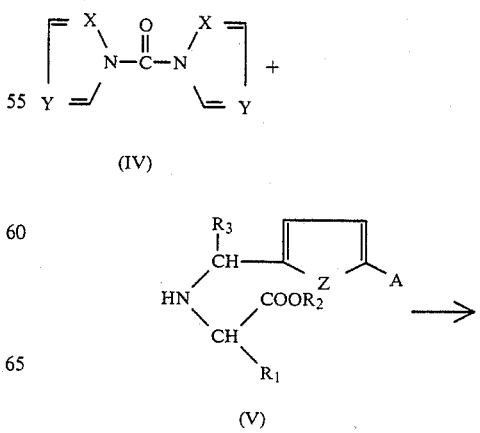

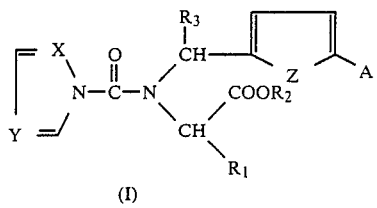

(I)

wherein $R_1$, $R_2$, $R_3$, A, X and Y are defined above.

The inert solvent used in the process (A) or (B) is an aromatic or aliphatic hydrocarbon or chlorinated aromatic or aliphatic hydrocarbon, for instance, benzene, toluene, xylene, chlorobenzene, dichlorobenzene, dichloromethane, 1,1,1-trichloroethane, chloroform, carbon tetrachloride, and the like or an ether, for instance, diethyl ether, dioxane and tetrahydrofuran.

In addition, a carbamoyl halide represented by the formula (II) can be obtained by reacting a secondary amine represented by the formula (V) with a carbonyl halide represented by the formula (VI) or (VII) in an inert solvent at a temperature of 0° to 150° C. for about 10 min to several hours:

$$CO(Hal)_2 \qquad (VI)$$

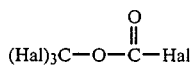 (VII)

wherein Hal is defined above.

A carbonylbisazole represented by the formula (IV) can be obtained by reacting an azole represented by the formula (III) with a carbonyl halide represented by the formula (VI) or (VII) in an inert solvent at a temperature of 0° to 100° C. for about 10 min to several hours, preferably, in the presence of a suitable acid-binding agent, for instance, a tertiary amine such as triethylamine and pyridine.

As a carbonyl halide represented by the formula (VI), phosgene is preferable, and as a compound represented by the formula (VII), trichloromethyl chloroformate is preferable. Azole represented by the formula (III) can be produced by a publicly known process, and imidazole, pyrazole and triazole may be mentioned as the examples thereof. In addition, a secondary amine represented by the formula (V) are produced by a process wherein an ester of halogenocarboxylic acid represented by the formula:

$$\underset{\text{Hal}-\overset{R_1}{\underset{|}{CH}}-COOR_2}{} \qquad (VIII)$$

wherein $R_1$ and $R_2$ are the same in the formula (I) and Hal is a halogen atom reacts with an amine represented by the general formula:

 (IX)

wherein $R_1$, A and Z are the same as in the general formula (I).

As an alkyl group of 1 to 6 carbon atoms represented by $R_2$ in the formula (I), a methyl group, ethyl group, propyl group, isopropyl group, butyl group, isobutyl group, secbutyl group, amyl group, hexyl group or the like may be mentioned.

As a halogen atom represented by Hal in the formula (II), a chlorine atom and bromine atom may be mentioned.

The representative compounds according to the present invention, which are produced in the above-mentioned processes, are shown in Table 1.

TABLE 1

Derivatives of N,N—substituted azolecarboxamide

Unit: °C. or $n_D^{25}$

| Compound No. | Structural formula | melting point or refractive index | Appearance |
|---|---|---|---|
| 1 | 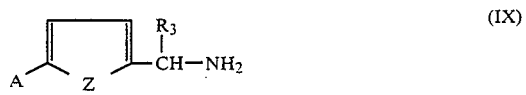 | m.p. 35–37° C. | pale yellow crystals |
| 2 | | $n_D^{25}$ 1.5154 | brownish yellow oily matter |
| 3 | | $n_D^{25}$ 1.5165 | pale yellow oily substance |

TABLE 1-continued

Derivatives of N,N—substituted azolecarboxamide

Unit: °C. or $n_D^{25}$

| Compound No. | Structural formula | melting point or refractive index | Appearance |
|---|---|---|---|
| 4 | (imidazole)-N(C=O)-N(CH₂-furyl)(CH₂COOC₂H₅) | $n_D^{25}$ 1.5144 | pale yellow oily substance |
| 5 | (imidazole)-N(C=O)-N(CH₂-furyl)(CH(CH₃)COOC₂H₅) | $n_D^{25}$ 1.5101 | pale yellow oily substance |
| 6 | (pyrazole)-N(C=O)-N(CH₂-furyl)(CH(CH₃)COOC₄H₉(n)) | $n_D^{25}$ 1.5103 | pale yellow oily substance |
| 7 | (pyrazole)-N(C=O)-N(CH₂-furyl)(CH(CH₃)COOCH₃) | $n_D^{25}$ 1.5238 | yellow oily substance |
| 8 | (pyrazole)-N(C=O)-N(CH₂-furyl)(CH(C₂H₅)COOCH₃) | m.p. 69–71° C. | pale yellow crystals |
| 9 | (pyrazole)-N(C=O)-N(CH₂-furyl)(CH(C₂H₅)COOC₃H₇(i)) | m.p. 52–53° C. | pale yellow crystals |
| 10 | (pyrazole)-N(C=O)-N(CH₂-furyl)(CH(CH₃)COOC₃H₇(n)) | $n_D^{25}$ 1.5140 | pale brown oily substance |
| 11 | (pyrazole)-N(C=O)-N(CH₂-furyl)(CH(CH₃)COOC₃H₇(i)) | m.p. 88–89° C. | pale yellow crystals |

TABLE 1-continued

Derivatives of N,N—substituted azolecarboxamide

| Compound No. | Structural formula | melting point or refractive index (Unit: °C. or $n_D^{25}$) | Appearance |
|---|---|---|---|
| 12 | [structure with CH₂COOCH₃] | m.p. 62–64° C. | pale yellow crystals |
| 13 | [structure with CH₂COOC₃H₇(iso)] | $n_D^{25}$ 1.5113 | pale yellow oily substance |
| 14 | [structure with CH₂COOC₄H₉(n)] | $n_D^{25}$ 1.5120 | pale brown oily substance |
| 15 | [structure with CHCOOC₄H₉(iso), CH₃] | $n_D^{25}$ 1.5080 | pale brown oily substance |
| 16 | [structure with CHCOOC₄H₉(sec), CH₃] | $n_D^{25}$ 1.5075 | pale yellow oily substance |
| 17 | [structure with CHCOOC₅H₁₁(n), CH₃] | $n_D^{25}$ 1.5084 | pale yellow oily substance |
| 18 | [structure with CHCOOC₅H₁₁(iso), CH₃] | $n_D^{25}$ 1.5082 | pale yellow oily substance |
| 19 | [structure with CHCOOC₆H₁₃(n), CH₃] | $n_D^{25}$ 1.5045 | pale yellow oily substance |

TABLE 1-continued

Derivatives of N,N—substituted azolecarboxamide

| Compound No. | Structural formula | melting point or refractive index (Unit: °C. or $n_D^{25}$) | Appearance |
|---|---|---|---|
| 20 | (imidazole)-N-C(=O)-N(CH$_2$-thienyl)(CH$_2$COOCH$_3$) | m.p. 69–72° C. | yellow crystals |
| 21 | (imidazole)-N-C(=O)-N(CH$_2$-thienyl)(CH$_2$COOC$_2$H$_5$) | m.p. 64–66° C. | pale yellow crystals |
| 22 | (imidazole)-N-C(=O)-N(CH$_2$-thienyl)(CH$_2$COOC$_3$H$_7$(iso)) | $n_D^{25}$ 1.5386 | pale yellow oily substance |
| 23 | (imidazole)-N-C(=O)-N(CH$_2$-thienyl)(CH(CH$_3$)COOCH$_3$) | $n_D^{25}$ 1.5478 | pale yellow oily substance |
| 24 | (imidazole)-N-C(=O)-N(CH$_2$-thienyl)(CH(CH$_3$)COOC$_2$H$_5$) | $n_D^{25}$ 1.5383 | pale yellow oily substance |
| 25 | (imidazole)-N-C(=O)-N(CH$_2$-thienyl)(CH(C$_2$H$_5$)COOC$_2$H$_5$) | $n_D^{25}$ 1.5389 | pale yellow oily substance |
| 26 | (imidazole)-N-C(=O)-N(CH$_2$-thienyl)(CH(C$_2$H$_5$)COOC$_3$H$_7$(iso)) | $n_D^{25}$ 1.5306 | pale yellow oily substance |
| 27 | (imidazole)-N-C(=O)-N(CH(CH$_3$)-thienyl)(CH(CH$_3$)COOC$_2$H$_5$) | $n_D^{25}$ 1.5394 | brown oily substance |

TABLE 1-continued

Derivatives of N,N—substituted azolecarboxamide

| Compound No. | Structural formula | melting point or refractive index Unit: °C. or $n_D^{25}$ | Appearance |
|---|---|---|---|
| 28 | | $n_D^{25}$ 1.5150 | yellow oily substance |
| 29 | | $n_D^{25}$ 1.5171 | yellow oily substance |
| 30 | | $n_D^{25}$ 1.5103 | yellow oily substance |

Among the present compounds represented by the formula (I), the preferable ones are those wherein $R_1$ is a methyl or ethyl group, $R_3$ and A are a hydrogen atom, X is a carbon atom and Y is a nitrogen atom. The more preferable ones are those wherein $R_1$ is a methyl or ethyl group, $R_3$ and A are a hydrogen atom, X is a carbon atom, Y is a nitrogen atom and Z is an oxygen atom. The most preferable ones are the compound of formula:

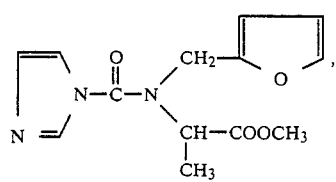

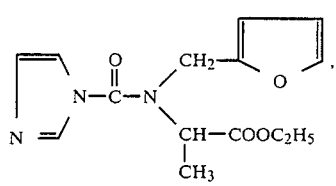

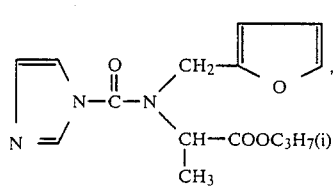

-continued

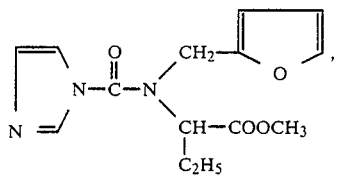

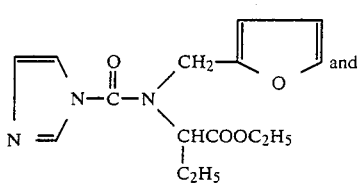 and

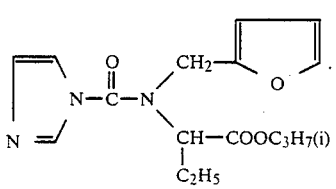

The process for producing the present compound is illustrated by the following examples:

EXAMPLE 1

Synthesis of N-(1-ethoxycarbonylethyl)-N-furfuryl-imidazole-1-carboxamide(Compound No. 2) by the process(B)

Into 100 ml of dry tetrahydrofuran in which 10 g (0.05 mol) of trichloromethyl chloroformate had been dissolved, 100 ml of dry tetrahydrofuran solution containing 13.6 g (0.2 mol) of imidazole and 10.1 g (0.1 mol) of triethylamine was added dropwise while maintaining at 0° to 10° C. After stirring the mixture for about one hour, 40 ml of dry tetrahydrofuran solution containing 19.7 g (0.1 mol) of N-(1-ethoxycarbonylethyl)-N-furfurylamine was slowly added dropwise while maintaining at 5° to 10° C. After heating the thus prepared mixture for one hour to reflux and then cooling the reaction mixture to room temperature, the cooled reaction mixture was poured into water, and the mixture was extracted with ethyl acetate. After washing the extract with water, the washed extract was treated by the usual procedures of separating, dehydrating and concentrating, and then purified by silica gel chromatography to obtain 16 g (0.055 mol) of an oily substance.

In the above-mentioned reaction procedures, by reacting at 50° C. for 6 hours instead of refluxing for one hour, the same oily substance was obtained. In addition, by using o-dichlorobenzene as the solvent instead of tetrahydrofuran and bringing the reactants into reaction at 150° C. for 40 min instead of refluxing for one hour, the aimed compound was also obtained as an oily substance. The physical constants of the thus obtained Compound No. 2 are as follows:

Infrared absorption spectrum(KBr): $\nu$ (cm$^{-1}$) 1700(C=O stretching, an absorption of an amide) and 1740(C=O stretching, an absorption of an ester).

Nuclear magnetic resonance spectrum(in CDCl$_3$): $\delta$ (ppm) 7.9(s, 1H) and 7.4(d, 2H): proton signal of imidazole ring and 7.0(s, 1H) and 6.35(s, 2H): proton signal of furan ring.

EXAMPLE 2

Synthesis of N-(ethoxycarbonylmethyl)-N-furfuryl-triazole-1-carboxamide (Compound No. 4) by the process(A)

Into a solution of 100 ml of dry tetrahydrofuran containing 10 g (0.05 mol) of trichloromethyl chloroformate, 30 ml of a dry tetrahydrofuran solution containing 13 g (0.071 mol) of N-(1-ethoxycarbonylmethyl)-N-furfurylamine was added dropwise while cooling the former at 0° to 5° C. After stirring the mixture for 30 min at room temperature, 200 ml of dry tetrahydrofuran solution containing 9.8 g (0.121 mol) of triazole was added at 10° to 15° C. to the mixture. Then the mixture was gradually heated to boiling and reacted for about one hour while refluxing. After the reaction was over, the reaction mixture was cooled to a room temperature and poured into water. The mixture was extracted with ethyl acetate, and the extract was treated by the usual procedures of washing with water, separating, dehydrating and concentrating. The thus obtained concentrate was subjected to silica gel chromatography to obtain 13 g (0.0468 mol) of an oily substance. The thus obtained Compound No. 4 gave the following physical constants:

Infrared absorption spectrum(KBr): $\nu$ (cm$^{-1}$), 1700(C=O stretching, an absorption of amide) 1740(C=O stretching, an absorption of ester).

Nuclear magnetic resonance spectrum(in CDCl$_3$): $\delta$ (ppm) 8.9(s, 1H) and 7.95(s, 1H): proton signal of triazole ring 7.4(s, 1H) and 6.4(d, 2H): proton signal of furan ring.

EXAMPLE 3

Synthesis of N-(1-ethoxycarbonylethyl)-N-(2-thiophenemethyl)-imidazole-1-carboxamide(Compound No. 24)

Into 100 ml of tetrahydrofuran solution containing 6.8 g (0.1 mol) of imidazole, 5.0 g (0.025 mol) of trichloromethyl chloroformate was added dropwise while maintaining the temperature of the solution at 0° to 10° C. under cooling, and then 5.1 g (0.05 mol) of triethylamine was added to the mixture. After stirring the mixture for one hour at room temperature, 10.7 g (0.05 mol) of N-(2-thiophenemethyl)-alanine ethyl ester was added, and the whole mixture was stirred for 2 hours while refluxing. The reaction mixture was thereafter cooled to room temperature and then poured into water. The mixture was extracted with ether, and the extract was subjected to the usual procedures of washing with water, separating, dehydrating and concentrating and further purifying through silica gel chromatographic column to obtain 10.8 g of the aimed compound (0.035 mol) as an oily substance. The physical constants of the thus obtained carboxamide were as follows:

Infrared absorption spectrum(KBr): $\nu$ (cm$^{-1}$) 1700(C=O stretching, an absorption of an amide) and 1730(C=O stretching, an absorption of an ester).

Nuclear magnetic resonance spectrum(in CDCl$_3$): $\delta$ (ppm) 8.0(S, 1H): proton signal of imidazole ring(1H), 7.4(m, 2H): proton signal of imidazole ring(1H), proton signal of thiophene ring(1H), 7.1(m, 3H): proton signal of imidazole ring(1H), proton signal of thiophene ring(2H).

EXAMPLE 4

Synthesis of N-(1-ethoxycarbonylethyl)-N-[1-(2-thienyl)-ethyl]-imidazole-1-carboxamide(Compound No. 27)

Into 50 ml of a toluene solution containing 8 g (0.04 mol) of trichloromethyl chloroformate, 4.3 g (0.054 mol) of pyridine was added dropwise while maintaining the solution at 0° to 10° C. under cooling with ice water, and 10.5 g (0.046 mol) of N-[1-(2-thienyl)-ethyl]alanine ethyl ester was added to the mixture. After stirring the whole mixture for 2 hours at room temperature, 80 ml of tetrahydrofuran solution containing 17 g (0.25 mol) of imidazole was added to the mixture, and the whole mixture was stirred for 3 hours while refluxing. After cooling the mixture to room temperature, it was poured into water and the mixture was extracted with ethyl acetate. The extract was treated by the ordinary procedures of water-washing, separating, dehydrating and concentrating followed by purifying through silica gel chromatographic column to obtain 5.2 g (0.016 mol) of the object product as an oily substance.

In the process mentioned above, by reacting at 50° C. for 8 hours instead of reacting for 3 hours while refluxing, the aimed product was obtained. In addition, by reacting at 150° C. in o-dichlorobenzene as a solvent instead of heating for 3 hours while refluxing in tetrahydrofuran as a solvent, the aimed product was obtained. The thus obtained Compound No. 27 gave the following physical constants:

Infrared absorption spectrum(KBr): $\nu$ (cm$^{-1}$) 1690(C=O stretching, an absorption of an amide), 1730(C=O stretching, an absorption of an ester).

Nuclear magnetic resonance spectrum(in CDCl$_3$): $\delta$ (ppm) 7.8(s, 1H): proton signal of imidazole ring(1H), 7.25(m, 2H): proton signal of imidazole ring(1H), proton signal of thiophene ring(1H), 6.9 (m, 3H): proton signal of imidazole ring(1H), proton signal of thiophene ring(2H).

REFERENCE EXAMPLE 1

Synthesis of N-(1-ethoxycarbonylethyl)-furfurylamine

To 19.4 g (0.2 mol) of furfurylamine maintained at 10° to 20° C. by ice-water cooling, 18.1 g (0.1 mol) of methyl α-bromopropionate was added dropwise. After stirring the reaction mixture at room temperature overnight, it was poured into water, and the thus formed oil was extracted with 100 ml of ethyl acetate. By washing the ethyl acetate solution with water, drying the ethyl acetate solution with anhydrous sodium sulfate, concentrating the dried ethyl acetate solution and distillating the concentrate under a vacuum, 16.2 g (0.082 mol) of oily substance was obtained. The thus obtained product was a colourless and transparent liquid boiling at 120° to 125° C. under a reduced pressure of 3 mmHg.

REFERENCE EXAMPLE 2

Synthesis of N-(2-thiophenemethyl)-alanine methyl ester

To 17.0 g (0.15 mol) of 2-thiophenemethylamine, 25 g (0.15 mol) of methyl α-bromopropionate was added, and 15.2 g (0.15 mol) of triethylamine was added dropwise to the mixture at a temperature of lower than 10° C. After stirring the mixture at room temperature overnight, 100 ml of water was added to the mixture, and the oily layer was extracted with 100 ml of ethyl acetate. By subjecting the extract to separating, drying, concentrating and distilling the resultant concentrate under a reduced pressure, 24.0 g (0.12 mol) of an oily substance was obtained. The thus obtained product was a pale yellow liquid boiling at 98° to 103° C. under a reduced pressure of 2 mmHg.

In the case where the present compound is used as a fungicide or a nematicide, it is directly used as it is, or is used in a form of compositions such as dusts, micro granule, granules, wettable powders, flowable compositions, emulsifiable concentrates and the like prepared by the usually adopted methods in a field of agrochemicals production while being mixed with at least one adjuvant in order to promote or stabilize the effects thereof.

These various compositions can be directly applied in fields as they are or applied after being diluted with water to a desired concentration.

As an adjuvant herein mentioned, a carrier (diluent) and the other adjuvants such as a sticker, an emulsifier, a wetting agent, a dispersant, a fixing agent, a disintegrator may be mentioned.

As a liquid carrier, an aromatic hydrocarbon such as toluene, xylene, an alcohol such as methanol, butanol, glycol, a ketone such as acetone, an amide such as dimethylformamide, a sulfoxide such as dimethylsulfoxide, and others such as methylnaphthalene, cyclohexane, animal and vegetable oils, fatty acids, esters of fatty acid may be mentioned.

As a solid carrier, clay, kaolin, talc, diatomaceous earth, silica, calcium carbonate, montmorillonite, bentonite, feldspar, quartz, alumina, sawdust and the like may be mentioned.

As an emulsifier or a dispersing agent, usually a surfactant is used and, for instance, anionic surfactants such as sodium higher alcohol sulfates, stearyltrimethyl ammonium chloride, polyoxyethylene alkylphenyl ether, laurylbetain, cationic surfactants, nonionic surfactants and amphoteric surfactants may be mentioned.

In addition, as a sticker, for instance, polyoxyethylene nonyl phenyl ether or polyoxyethylene lauryl ether may be mentioned, and as a wetting agent, for instance, polyoxyethylene nonyl phenyl ether or dialkyl sulfosuccinate may be mentioned. As a fixing agent, carboxymethylcellulose or polyvinyl alcohol, and as a disintegrator, sodium ligninsulfonate or sodium lauryl sulfate may be mentioned.

Every composition containing the present compound as the active ingredient is not only singly applicable singly, but also applicable after mixing with other fungicides, insecticides, plant growth regulators, miticides, herbicides, fungicides for soil, soil-improving agents or nematicides and furthermore, it is applicable after mixing with fertilizers.

The content of the present compound as the active ingredient in the fungicidal composition or the nematicidal composition for agricultural or horticultural use depends on the form and shape of the composition, the method for application and other conditions, and although there are cases where the present compound itself is the sole component, the content is usually in a range of 0.5 to 95% by weight, preferably in the range of 2 to 70% by weight.

The fungicidal composition or nematicidal composition for agricultural or horticultural use according to the present invention is applied on foliage of crop plants or in soil where crop plants are grown, and shows an excellent controlling effects against crop diseases, and particularly, to the diseases on the above-ground part of the crop plants such as powdery mildew, scab, grey mold by application into the soil where the crop plants are grown. In addition, the nematicidal composition according to the present invention shows a remarkable nematicidal effect against rice white-tip nematode, chrysanthemum foliar nematode, root-knot nematodes, lesion nematodes, cyst nematodes, pine wood nematode and the like, and accordingly, can be applied for controlling effectively these nematodes.

In cases of practical application, it is preferable to scatter the composition at a concentration of the active ingredient of 10 to 4,000 ppm onto leaves and stems, and in cases of soil application, the amount is preferably 0.05 to 10 kg per 10 areas.

The fungicidal or nematicidal composition for agricultural or horticultural use according to the present invention is illustrated by the following examples, and in this case, the kinds and the ratio of mixing thereof with the active ingredient are not restricted to the Examples and are changable in a broad range. In Examples, "part" means part by weight.

FORMULATION EXAMPLE 1

Dust

Ten parts of Compound No. 1, N-(1-ethoxycarbonylmethyl)-N-(2-furfuryl)-imidazole-1-carboxamide, 41 parts of talc and 49 parts of clay were mixed and by pulverizing the resultant mixture, a dust was prepared.

FORMULATION EXAMPLE 2

Wettable powder

Eighty parts of Compound No. 2, N-(1-ethoxycarbonylethyl)-N-(2-furfuryl)-imidazole-1-carboxamide, 15 parts of kaolin, 3 parts of sodium higher alcohol sulfate and 2 parts of sodium polyacrylate were mixed and by pulverizing the resultant mixture, a wettable powder was prepared.

FORMULATION EXAMPLE 3

Granule

Three parts of Compound No. 5, N-(1-ethoxycarbonylethyl)-N-(2-furfuryl)-triazole-1-carboxamide, 35 parts of diatomaceous earth, 23 parts of bentonite, 37 parts of talc and 2 parts of a disintegrator were mixed and then 18 parts of water was added to the mixture to wet the components uniformly and afterwards the mixture was subjected to an injection molding machine to be extruded as granules. After drying the granules, they were subjected to a crusher and then to a granulator to obtain a granule of size of 0.6 to 1 mm.

FORMULATION EXAMPLE 4

Micro granule

Five parts of Compound No. 3, N-(1-ethoxycarbonylethyl)-N-(2-furfuryl)-pyrazole-1-carboxamide, 6 parts of bentonite and 9 parts of clay were uniformly mixed and the resultant mixture was pulverized to be a dense dust composition. Separately, 80 parts of non-oil absorbent coarse mineral powder of 105–74μ was introduced into a suitable mixer and while rotating the mixer, 20 parts of water was introduced into the mixer and after uniformly wetting the mineral matter, the dense dust composition prepared above was introduced into the mixer and then the dense dust composition was covered with the above mineral material to obtain the micro granule.

FORMULATION EXAMPLE 5

Emulsion

Twenty parts of Compound No. 2, N-(1-ethoxycarbonylethyl)-N-(2-furfuryl)-imidazole-1-carboxamide was dissolved in 63 parts of xylene, and 17 parts of a 8:2 mixture of a condensate of alkylphenol and ethylene oxide and calcium alkylbenzenesulfonate was added to the solution to be dissolved therein to obtain an emulsion.

The excellent effect of the present compound in controlling diseases and nematodes on crop plants of agriculture and horticulture is illustrated by the following experimental examples:

EXPERIMENTAL EXAMPLE 1

Cucumber powdery mildew-controlling test

Each of the emulsions of FORMULATION EXAMPLE 5 and emulsion obtained by using Compound No. 7, 11, 21, 24–28 or 29 instead of Compound No. 2 in FORMULATION EXAMPLE 5 was diluted by water to contain each active ingredient at 250 ppm, and was applied onto the potted cucumber seedlings (variety: $F_1$Kyoryoku green fushinari, at the stage of first leaf-developing).

After drying, the cucumber seedlings were inoculated by spraying the spore suspension of *Sphaerotheca fuliginea*, and after keeping the planted pots in a greenhouse for 2 weeks, the disease degree was investigated then disease index and control value were calculated according to the following formula. As a positive control, thiophanatemethyl 70% wettable powder {active ingredient: 1,2-bis(3-methoxycarbonyl-2-thioureide)-benzene} was used after diluting with water at a concentration of 350 ppm.

$$\text{Disease Index} = \frac{(3 \times A) + (2 \times B) + (1 \times C)}{3 \times (A + B + C + D)} \times 100$$

wherein A:
number of plants on which severe disease occurrence was observed,
B: number of plants on which considerable disease was observed,
C: number of plants on which slight disease was observed,
D: number of plants without disease.

From the thus recorded index of disease, the control value of each fungicidal specimen was calculated according to the following formula:

$$\text{Control value} = \frac{\begin{array}{c}(\text{Disease Index in the} \\ \text{not-treated plot})\end{array} - \begin{array}{c}(\text{Disease Index in} \\ \text{the treated plot})\end{array}}{(\text{Disease Index in the not-tresated plot})}$$

The results of the test are shown in Table 2.

TABLE 2

Test results of Cucumber powdery mildew-controlling

| Tested compound | Concentration (ppm) | Control value | Phytotoxicity |
|---|---|---|---|
| No. 2 | 250 | 100 | no |
| No. 7 | 250 | 100 | no |
| No. 8 | 250 | 100 | no |
| No. 9 | 250 | 100 | no |
| No. 10 | 250 | 100 | no |
| No. 11 | 250 | 100 | no |
| No. 21 | 250 | 60 | no |
| No. 24 | 250 | 55 | no |
| No. 25 | 250 | 80 | no |
| No. 26 | 250 | 100 | no |
| No. 27 | 250 | 100 | no |
| No. 28 | 250 | 60 | no |
| No. 29 | 250 | 55 | no |
| control* | 350 | 40 | no |

Note: control: Thiophanatemethyl 70% wettable powder.

EXPERIMENTAL EXAMPLE 2

Cucumber Scab-controlling test

Each of the emulsions of FORMULATION EXAMPLE 5 and emulsion obtained by using Compound No. 11, 16, 23, 25, 26 or 27 instead of Compound No. 2 in FORMULATION EXAMPLE 5, was diluted with water to contain each active ingredient at 500 ppm, and applied onto the potted cucumber seedlings (variety: Tokiwa jibai, at the stage of first leaf-developing).

After drying, the cucumber seedlings were inoculated by spraying the spore suspension of *Cladosporium cucumerinum*, and after one day of keeping the planted pots in a wet chamber at 20° C., the planted pots were kept in a greenhouse. The disease degree on the plants was investigated 7 days after inoculation to calculate the control value of each compound according to the formulae shown in EXPERIMENTAL EXAMPLE 1.

The results of the test are shown in Table 3.

TABLE 3

Test results of Cucumber scab-controlling

| Tested compound | Concentration (ppm) | Control value | phytotoxicity |
|---|---|---|---|
| No. 2 | 500 | 80 | no |
| No. 11 | 500 | 85 | no |
| No. 16 | 500 | 80 | no |
| No. 23 | 500 | 75 | no |
| No. 25 | 500 | 70 | no |

TABLE 3-continued

Test results of Cucumber scab-controlling

| Tested compound | Concentration (ppm) | Control value | phytotoxicity |
| --- | --- | --- | --- |
| No. 26 | 500 | 85 | no |
| No. 27 | 500 | 85 | no |
| not-treated | — | 0 | — |

EXPERIMENTAL EXAMPLE 3

Kidney bean gray mold-controlling test

Each of the emulsions of FORMULATION EXAMPLE 5 and emulsion obtained by using Compound No. 11, 16, 18, 22, 24, 26 or 27 instead of Compound No. 2 of FORMULATION EXAMPLE 5, was diluted with water to contain each active ingredient at 500 ppm, and thus obtained solution was applied onto the potted deedlings of kidney bean plant (variety: Shin-edogawa, at the stage of primary leaf-developing.

After drying, a piece of cultured myceria of *Botrytis cinerea* cut out from the culture by a cork-borer of 5 mm in diameter was placed on the primary leaf, and the thus treated plants were kept at a moist chamber to be infected. After 48 hours of the inoculation, the lesion diameter on the primary leaf was investigated to calculate the control value of each compound according to the following formula.

$$\text{Control value} = \frac{(\text{Lesion diameter in the non-treated plot}) - (\text{Lesion diameter in each treated plot})}{(\text{Lesion diameter in the non-treated plot})} \times 100$$

The results are shown in Table 4.

TABLE 4

Test Results of Kidney bean Gray mold-Controlling

| Tested compounds | Concentration (ppm) | Control value | Phytotoxicity |
| --- | --- | --- | --- |
| No. 2 | 500 | 100 | no |
| No. 18 | 500 | 90 | no |
| No. 22 | 500 | 70 | no |
| No. 24 | 500 | 70 | no |
| No. 26 | 500 | 80 | no |
| No. 27 | 500 | 85 | no |

EXPERIMENTAL EXAMPLE 4

Cucumber Damping-off-controlling test

Field soil was packed in unglazed pots of 12 cm in diameter, and on the potted soil, each 5 g of pathogenic soil in which *Rhizoctonia solani* had been cultured was uniformly inoculated to the field soil.

Seeds of cucumber (variety: F₁ Kyoryoku green fushinari) were sown on the thus potted soil at 10 seeds/pot, and each of the emulsions of FORMULATION EXAMPLE 5 and emulsion obtained by using Compound No. 6, 9–10 or 11 instead of Compound No. 2 of FORMULATION EXAMPLE 5, was diluted with water and the thus diluted solution was drenched to the thus potted soil in an amount of 50 ml per pot, and the drenched pots were kept in a greenhouse. As a control, captan 80% wettable powder (active ingredient: N-trichloromethylthiotetrahydrophthalimide) was used after diluting with water to the same concentration.

After 10 days of sowing the seed, the state of disease was investigated, and the percentage of the healthy seedlings of each plot was calculated according to the following formula.

$$\text{Percentage of healthy seedlings} = \frac{(\text{Number of healthy seedlings in each plot})}{(\text{Number of healthy seedlings in the not-treated and not-inoculated plot})} \times 100$$

The results of the test are shown in Table 5.

TABLE 5

Test Results of Cucumber Damping-off Controlling

| Tested compound | Amount of compound per pot(g: active ingredient) | Percentage of healthy seedlings | Phytotoxicity |
| --- | --- | --- | --- |
| No. 2 | 0.05 | 85.0 | no |
| No. 6 | 0.05 | 80.0 | no |
| No. 9 | 0.05 | 80.0 | no |
| No. 10 | 0.05 | 85.0 | no |
| No. 11 | 0.05 | 80.0 | no |
| Control* | 0.05 | 75.0 | no |
| Control | — | 14.2 | — |

Note: *captan 80% wettable powder.

EXPERIMENTAL EXAMPLE 5

Cucumber powdery mildew-controlling test by soil treatment

The seedlings of cucumber (variety: Tokiwa jibai, at the stage of first leaf developing) grown on the potted soil in a pot of 10 cm in diameter, was drenched with the diluted solution of each of the emulsion of FORMULATION EXAMPLE 5 and emulsion obtained by using Compound No. 7–11, 20, 22–26 or 27 instead of Compound No. 2 of FORMULATION EXAMPLE 5, at a rate of 25 ml per pot (the amount of each active ingredient per pot was 0.0125 g).

As the control, 12.5% liquid formulation contains N-(ethoxycarbonylmethyl)-N-(4-chlorophenyl)-imidazole-1-carboxamide or dimethirimol (5-butyl-2-dimethylamino-6-methylpyrimidine-4-ol) 12.5% was used.

After three days of the soil treatment, the seedlings were inoculated by spores of *Sphaerotheca fuliginea*, and after keeping the pots in a greenhouse for 2 weeks, disease degree on the seedlings was investigated and the control value of each active-ingredient was calculated according to the formulae in EXPERIMENTAL EXAMPLE 1. The results are shown in Table 6.

TABLE 6

Test Results of Cucumber powdery mildew controlling by soil treatment

| Tested compound | Amount of compound per pot (g: active ingredient) | Control value | Phytotoxicity |
| --- | --- | --- | --- |
| No. 2 | 0.0125 | 100 | no |
| No. 7 | 0.0125 | 50 | no |
| No. 8 | 0.0125 | 90 | no |
| No. 9 | 0.0125 | 50 | no |
| No. 10 | 0.0125 | 50 | no |
| No. 11 | 0.0125 | 90 | no |
| No. 20 | 0.0125 | 55 | no |
| No. 22 | 0.0125 | 55 | no |
| No. 23 | 0.0125 | 60 | no |
| No. 24 | 0.0125 | 70 | no |
| No. 25 | 0.0125 | 55 | no |
| No. 26 | 0.0125 | 100 | no |
| No. 27 | 0.0125 | 100 | no |
| control 1 | 0.0125 | 5 | no |
| control 2 | 0.0125 | 50 | no |

TABLE 6-continued

Test Results of Cucumber powdery mildew controlling by soil treatment

| Tested compound | Amount of compound per pot (g: active ingredient) | Control value | Phytotoxicity |
|---|---|---|---|
| not-treated | — | 0 | — |

Notes:
control 1: N—(ethoxycarbonylmethyl)-N—(4-chlorophenyl)-imidazole-1-carboxamide (Japanese Patent Laid-open Publication No. 31047/1975) 12.5% liquid formulation.
control 2: Dimethirimol 12.5% liquid formulation.

EXPERIMENTAL EXAMPLE 6

Cucumber scab-controlling test by soil treatment

Each of the wettable powders of FORMULATION EXAMPLE 2 and wettable powder obtained by using Compound No. 7 instead of Compound No. 2 of FORMULATION EXAMPLE 2, was diluted with water, and each of the diluted solution was applied to the soil of the cucumber seedlings (variety: Tokiwa jibai, at the stage of first leaf developing) grown in the potted soil in a pot having diameter of 10 cm at a rate of 25 ml/pot.

After one day of the soil treatment, a spore suspension of *Cladosporium cucumerinum* was sprayed onto the seedlings, and after keeping the potted plants in a moist chamber at 20° C. for one day, the pots were transferred to a greenhouse to accelerate the disease occurrence. The state of disease on the seedlings was investigated after 7 days of inoculation to calculate the control value of each active ingredient according to the formulae in EXPERIMENTAL EXAMPLE 1. The results are shown in Table 7.

TABLE 7

| Tested compound | Amount of compound per pot (g: active ingredient) | Control value | Phytotoxicity |
|---|---|---|---|
| No. 2 | 0.03 | 100 | no |
| No. 2 | 0.015 | 100 | no |
| No. 7 | 0.03 | 80 | no |
| No. 7 | 0.015 | 60 | no |
| not-treated | — | 0 | — |

EXPERIMENTAL EXAMPLE 7

Cucumber gray mold-controlling test by soil application

Each of the emulsions of FORMULATION EXAMPLE 5 and emulsion obtained by using Compound No. 7 instead of Compound No. 2 of FORMULATION EXAMPLE 5, was diluted with water, and each of thus obtained solutions was applied to the soil around the cucumber seedlings (F1 Kyoryoku green fushinari, at the stage that the first leaf is developing) grown in the soil in a pot having diameter of 10 cm at the rate of 25 ml/pot, after 3 days, a piece of myceria of *Botrytis cinerea* cultured in a Petri dish and cut out by a cork borer of 5 mm in diameter was placed on the first leaf of each seedling, and the potted plants were kept in a moist chamber state to accelerate the disease. The lesion diameter observed around the piece of myceria on the first leaf was investigated after 48 hours of inoculation to calculate the control value according to the formulae in EXPERIMENTAL EXAMPLE 3.

The results are shown in Table 8.

TABLE 8

| Tested compound | Amount of compound per pot(g: active ingredient) | Control value | Phytotoxicity |
|---|---|---|---|
| No. 2 | 0.03 | 100 | no |
| No. 2 | 0.015 | 100 | no |
| No. 7 | 0.03 | 85 | no |
| No. 7 | 0.015 | 75 | no |
| Not-treated | — | 0 | — |

EXPERIMENTAL EXAMPLE 8

Cucumber Fusarium wilt-controlling test

Field soil was packed in unglazed pots of 12 cm in diameter, and on the thus potted soil, each 15 g of pathogenic soil in which *Fusarium oxysporum* f. *sp. cucumerinum* had been cultured was uniformly placed per pot to inoculate the field soil in the pot. Thereafter, seeds of cucumber (variety: Kyoryoku green fushinari) were sown at 10 seeds/pot.

The emulsion prepared in FORMULATION EXAMPLE 5 containing Compound No. 2 was diluted with water and the diluted emulsion was applied onto the potted seedlings at a rate of 50 ml/pot.

The potted plants were kept in a greenhouse with the control treated by benomyl 50% wettable powder, and after 10 days of sowing, the state of disease occurrence on the seedlings was investigated to calculate the percentage of healthy seedlings according to the formulae in EXPERIMENTAL EXAMPLE 4.

The results are shown in Table 9.

TABLE 9

| Tested compound | Amount of compound per pot (g: active ingredient) | Percentage of healthy seedling | Phytotoxicity |
|---|---|---|---|
| No. 2 | 0.025 | 85 | no |
| Control | 0.025 | 50 | no |
| not-treated | — | 0 | — |

Note: Control: benomyl 50% wettable powder.

EXPERIMENTAL EXAMPLE 9

Controlling test of storage diseases of citrus

Oranges were dipped in a diluted emulsion, in which the emulsion was prepared in FORMULATION EXAMPLE 5 and diluted with water. After air-drying the fruits and then injuring the fruits with a test needle, a spore suspension of *Penicillium italicum* was sprayed onto the thus stung fruits and kept in a moisture chamber to be infected.

As a control, thiophanatemethyl 70% wettable powder containing 1,2-bis(3-methoxycarbonyl-2-thioureido)benzene was used. The fungicidal effect was judged by the area of lesion on the fruit. The results are shown in Table 10.

TABLE 10

| Tested compound | Concentration | percentage lesion area | Phytotoxicity |
|---|---|---|---|
| No. 2 | 500 | 0 | no |
| Control | 1000 | 10 | no |
| not-treated | — | 90 | — |

Note: Control: thiophanatemethyl 70% wettable powder.

EXPERIMENTAL EXAMPLE 10

Antifungal activity test in vitro

Agar plates each containing one of the present compounds No. 1, No. 2, No. 3 and No. 5 at a predeterminated concentration were prepared by the method of agar-plate dilution using a potato-agar culture medium, and each of the pathogenic fungi shown in Table 11 was inoculated on the thus prepared agar plates. After culturing each fungus for 5 days at 25° C., the minimum growth inhibitory concentration (MIC) of each of the present compounds was determined by the usual method.

The results are shown in Table 11.

TABLE 11

| | MIC unit: microgram/ml | | | |
|---|---|---|---|---|
| | Compounds tested | | | |
| Fungal species | No. 1 | No. 2 | No. 3 | No. 5 |
| Penicillium italicum | 20 | 1 | >500 | 100 |
| Pythium aphanidermatum | >500 | >500 | 500 | 500 |
| Pyricularia oryzae | 100 | 20 | 100 | 20 |
| Helminthosporium oryzae | 500 | 20 | >500 | 500 |
| Botrytis cinerea | 500 | 20 | >500 | >500 |
| Verticillium albo-atrum | 100 | 4 | >500 | 100 |

The numerical figures in Table 11 are MIC (microgram/ml), and the values less than 50 mean strong antifungal activity; the values between 50 and 250 mean fairly strong antifungal activity and the values between 250 and 500 mean moderate antifungal activity.

EXPERIMENTAL EXAMPLE 11

Antifungal activity test in vitro

The same test as in EXPERIMENTAL EXAMPLE 10 was carried out while using *Verticillium albo-atrum* as a pathogenic fungus, and respective compounds Nos. 2, 6, 7 and 8, the results being shown in Table 12.

TABLE 12

| Tested compounds | MIC(microgram/ml) |
|---|---|
| No. 2 | 4 |
| No. 6 | 20 |
| No. 7 | 20 |
| No. 8 | 20 |

EXPERIMENTAL EXAMPLE 12

Controlling test against Verticillium wilt on eggplant

Each of the emulsions of FORMULATION EXAMPLE 5 and emulsion obtained by using Compound Nos. 11, 21, 23, 24–26 or 27 instead of Compound No. 2 of FORMULATION EXAMPLE 5, was diluted with water, and it was applied into the soil in the pot at a rate of 50 ml per pot where eggplant (variety: Senryo No. 2, at the stage of 5 to 6 leaves) had been grown. Afterwards, a spore suspension of *Verticillium albo-atrum* was injected into the stem of the eggplant to inoculate the plant. After 10 days of inoculation, the disease index was investigated and the index of disease and the control value were calculated according to the following formulae. As a positive control, benomyl 50% wettable powder containing methyl 1-(butylcarbamoyl)-2-benzimidazolecarbamate as the active ingredient was used after diluting with water.

$$\text{Disease Index} = \frac{(4 \times A) + (3 \times B) + (2 \times C) + D}{4 \times (A + B + C + D + E)} \times 100$$

wherein A: number of plants on which lesion was observed on more than ⅔ of the leaves thereof, B: number of plants on which lesion was observed on ½ to ⅔ of the leaves thereof, C: number of plants on which lesion was observed on ⅓ to ½ of the leaves thereof, D: number of plants on which lesion was observed on less than ⅓ of the leaves thereof and E: number of plants without lesion on the leaves thereof.

$$\text{Control value} = \frac{\left(\begin{array}{c}\text{Disease Index in}\\\text{the not-treated plot}\end{array}\right) - \left(\begin{array}{c}\text{Disease Index in}\\\text{the treated plot}\end{array}\right)}{\left(\begin{array}{c}\text{Disease Index in}\\\text{the not-treated plot}\end{array}\right)} \times 100$$

The test results are shown in Table 13.

TABLE 13

Results of Verticillium wilt-controlling on eggplant

| Tested compounds | Amount of compound per pot (g: active ingredient) | Control value | Phytotoxicity |
|---|---|---|---|
| No. 2 | 0.02 | 100 | no |
| No. 11 | 0.02 | 100 | no |
| No. 21 | 0.02 | 85 | no |
| No. 23 | 0.02 | 90 | no |
| No. 24 | 0.02 | 90 | no |
| No. 25 | 0.02 | 85 | no |
| No. 26 | 0.02 | 95 | no |
| No. 27 | 0.02 | 95 | no |
| Positive control | 0.02 | 80 | no |
| not-treated | — | 0 | — |

Note: Positive control: benomyl 50% wettable powder.

EXPERIMENTAL EXAMPLE 13

Controlling test against tomato root-knot nematode

After mixing soil infested by *Meloidogyne incognita* with 0.1 g of each of the 10% dusts of FORMULATION EXAMPLE 1 and dusts which were obtained by the same method as in FORMULATION EXAMPLE 1 using Compound Nos. 1–9, 20, 22, 24–27 respectively as an active ingredient instead of Compound No. 1 of FORMULATION EXAMPLE 1, the mixture was packed in an unglazed pot of 12 cm in diameter. The seeds of tomato (variety: Ponte Rosa) was sown in the potted soil at 15 seeds/pot.

After 40 days of the soil-treatment, the seedlings of tomato were dug out from the potted soil, and the phytotoxicy and the gall index were investigated according to the following formula:

$$\text{gall index} = \frac{(4 \times A) + (3 \times B) + (2 \times C) + D}{4 \times \text{(total number of seedlings)}} \times 100$$

wherein A: number of seedlings each having more than 31 galls on the roots thereof, B: number of seedlings each having 21 to 30 galls on the roots thereof, C: number of seedlings each having 11 to 20 root-knots on the roots thereof and D: number of seedlings each having 1 to 10 galls on the roots thereof. The results are shown in Table 14.

TABLE 14

Results of controlling root-knot nematode on tomato

| Tested compound | Amount of compound per pot (g) | gall index | Phytotoxicity |
|---|---|---|---|
| No. 1 | 0.01 | 20 | no |
| No. 2 | 0.01 | 10 | no |
| No. 3 | 0.01 | 35 | no |
| No. 4 | 0.01 | 60 | no |
| No. 5 | 0.01 | 55 | no |
| No. 6 | 0.01 | 20 | no |
| No. 7 | 0.01 | 15 | no |
| No. 8 | 0.01 | 25 | no |
| No. 9 | 0.01 | 65 | no |
| No. 20 | 0.01 | 60 | no |
| No. 22 | 0.01 | 55 | no |
| No. 24 | 0.01 | 30 | no |
| No. 25 | 0.01 | 40 | no |
| No. 26 | 0.01 | 20 | no |
| No. 27 | 0.01 | 20 | no |
| not-treated | — | 100 | — |

EXPERIMENTAL EXAMPLE 14

Controlling test on cucumber root-knot nematode

In the field infested by *Meloidogyne incognita*, seedlings of cucumber (variety: $F_1$ green) were transplanted at the five leaf-stage. 10 days after planting, a diluted emulsion with water of the 20% emulsion containing Compound No. 2 prepared in FORMULATION EXAMPLE 5 was drenched into the soil at 200 ml/plant.

After 40 days of the treatment, the seedlings were dug out from the ground to observe the phytotoxicity and calculate the gall index (according to EXPERIMENTAL EXAMPLE 13). The results are shown in Table 15.

TABLE 15

Results of controlling root-knot nematode

| Tested compound | Concentration of compound in application (ppm) | gall index | Phytotoxicity |
|---|---|---|---|
| No. 2 | 125 | 14 | no |
| No. 2 | 250 | 16 | no |
| No. 2 | 500 | 12 | no |
| not-treated | — | 100 | — |

What is claimed is:

1. A derivative of N,N-substituted azolecarboxamide represented by the formula:

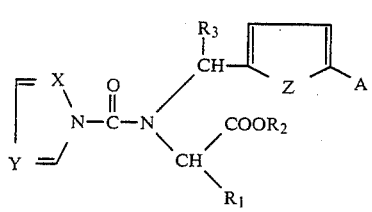

(I)

wherein $R_1$ represents a hydrogen atom, methyl group or ethyl group or propyl group; $R_2$ represents an alkyl group of 1 to 6 carbon atoms; $R_3$ represents a hydrogen atom or methyl group; A represents a hydrogen atom or methyl group; X and Y represent respectively a carbon atom or nitrogen atom, provided that when X represents a nitrogen atom, Y represents a nitrogen atom or a carbon atom and when X represents a carbon atom, Y represents a nitrogen atom; and Z represents an oxygen atom or sulfur atom, provided that when Z represents a sulfur atom, A represents only a hydrogen atom.

2. The derivative according to claim 1, wherein $R_1$ represents a methyl group or ethyl group, $R_3$ and A represent a hydrogen atom, X represents a carbon atom, and Y represents a nitrogen atom.

3. The derivative according to claim 2, wherein Z is an oxygen atom.

4. The derivative according to claim 3, which is represented by the formula:

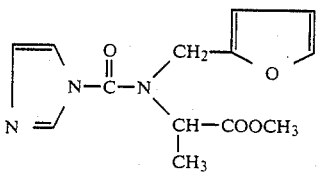

5. The derivative according to claim 1, which is represented by the formula:

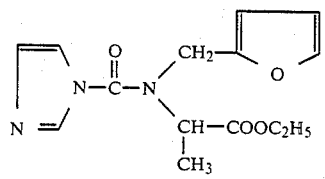

6. The derivative according to claim 1, which is represented by the formula:

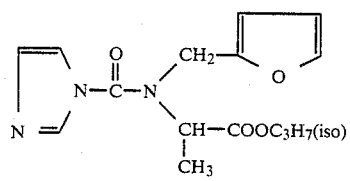

7. The derivative according to claim 1, which is represented by the formula:

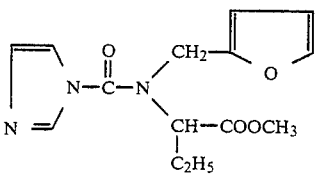

8. The derivative according to claim 1, which is represented by the formula:

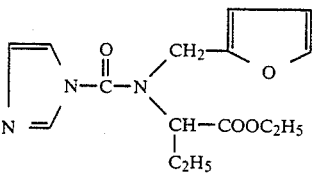

9. The derivative according to claim 1, which is represented by the formula:

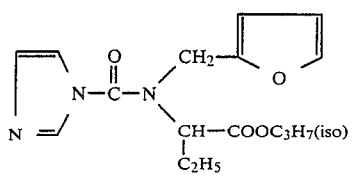

10. A fungicidal or nematicidal composition, which comprises 0.5–95% by weight of a compound of the formula (I) as active ingredients and 5–99.5% by weight of adjuvant.

11. A method for preventing diseases of agricultural or horticultural plants caused by fungi, comprising applying to soil or said plants a fungicidally effective amounts of a compound of the formula (I).

12. A method for combatting nematodes, comprising applying to soil or plants a nematocidally effective amount of a compound of the formula (I).

* * * * *

UNITED STATES PATENT AND TRADEMARK OFFICE
CERTIFICATE OF CORRECTION

PATENT NO. : 4,500,536

DATED : February 19, 1985

INVENTOR(S) : Hiroshi Yoshida, et al.

It is certified that error appears in the above-identified patent and that said Letters Patent is hereby corrected as shown below:

In the abstract, in the fifth and sixth lines after the formula (one occurrence) and in the eighth line after the formula "a carbon atom" should read —CH—. In the abstract, in the eighth line after the formula "carbon atom" (first occurrence) should read —CH—.

Column 1, in the fifth and sixth lines after the formula (one occurrence) and in the eighth line after the formula "a carbon atom" should read —CH—. Column 1, in the eighth line after the formula "carbon atom" (first occurrence) should read —CH—.

Column 2, line 5 delete "and" after the word "giving" and substitute therefor —any—.

Column 11, lines 38 and 40-41 "a carbon atom" should read —CH—.

Column 19, lines 18-19 delete "deedlings" and substitute therefor —seedlings—.

Claim 1, in the fifth and sixth lines after the formula (one occurrence) and in the eighth line after the formula "a carbon atom" should read —CH—. Claim 1, in the eighth line after the formula "carbon atom" (first occurrence) should read —CH—.

UNITED STATES PATENT AND TRADEMARK OFFICE
CERTIFICATE OF CORRECTION

PATENT NO. : 4,500,536

DATED : February 19, 1985

INVENTOR(S) : Hiroshi Yoshida, et al

It is certified that error appears in the above-identified patent and that said Letters Patent is hereby corrected as shown below:

Claim 2, line 3 "a carbon atom" should read --CH--.

Signed and Sealed this

Twenty-eighth Day of January 1986

[SEAL]

Attest:

Attesting Officer

DONALD J. QUIGG

Commissioner of Patents and Trademarks